US009913651B2

(12) United States Patent
Fogarty et al.

(10) Patent No.: US 9,913,651 B2
(45) Date of Patent: Mar. 13, 2018

(54) EMBOLIZATION DEVICE AND A METHOD OF USING THE SAME

(71) Applicants: Thomas J. Fogarty, Portola Valley, CA (US); Michael J. Drews, Palo Alto, CA (US); D. Bruce Modesitt, San Carlos, CA (US); Neil D. Holmgren, Chicago, IL (US); David B. Willis, Palo Alto, CA (US)

(72) Inventors: Thomas J. Fogarty, Portola Valley, CA (US); Michael J. Drews, Palo Alto, CA (US); D. Bruce Modesitt, San Carlos, CA (US); Neil D. Holmgren, Chicago, IL (US); David B. Willis, Palo Alto, CA (US)

(73) Assignee: Thomas J. Fogarty, Mountain View, CA (US)

( * ) Notice: Subject to any disclaimer, the term of this patent is extended or adjusted under 35 U.S.C. 154(b) by 44 days.

(21) Appl. No.: 14/990,666

(22) Filed: Jan. 7, 2016

(65) Prior Publication Data

US 2016/0113658 A1 Apr. 28, 2016

Related U.S. Application Data

(60) Continuation of application No. 14/657,888, filed on Mar. 13, 2015, now Pat. No. 9,629,636, which is a
(Continued)

(51) Int. Cl.
*A61F 2/958* (2013.01)
*A61B 17/12* (2006.01)
(Continued)

(52) U.S. Cl.
CPC .... *A61B 17/12118* (2013.01); *A61B 17/1214* (2013.01); *A61B 17/12022* (2013.01);
(Continued)

(58) Field of Classification Search
CPC .............. A61B 17/12; A61B 17/12109; A61B 17/12118; A61B 17/1214;
(Continued)

(56) References Cited

U.S. PATENT DOCUMENTS 2,903,365 A   9/1959   O'Brian et al.
4,085,757 A   4/1978   Pevsner
(Continued)

FOREIGN PATENT DOCUMENTS

AU   2003/204493   12/2003
FR   2689388        7/1999
(Continued)

OTHER PUBLICATIONS

Franklin et al, "Uptake of Tetracycline by Aortic Aneurysm Wall and Its Effect on Inflammation and Proteolysis;" *Brit. J. Surgery*, 86(6):771-775, 1999.
(Continued)

*Primary Examiner* — Victor Nguyen
(74) *Attorney, Agent, or Firm* — Levine Bagade Han LLP

(57) ABSTRACT

Non-expandable space-occupying devices for treating voids within the body are disclosed. The devices can have multiple non-expandable space-occupying elements connected to a flexible leader. Methods of making and using the devices are also disclosed.

8 Claims, 12 Drawing Sheets

Related U.S. Application Data continuation of application No. 14/058,986, filed on Oct. 21, 2013, now Pat. No. 9,005,235, which is a continuation of application No. 13/569,348, filed on Aug. 8, 2012, now Pat. No. 8,562,636, which is a division of application No. 12/340,483, filed on Dec. 19, 2008, now Pat. No. 8,262,686, which is a continuation of application No. 10/293,139, filed on Nov. 12, 2002, now Pat. No. 7,481,821.

(51) Int. Cl.

| | | |
|---|---|---|
| *A61B 90/00* | (2016.01) | |
| *A61F 2/07* | (2013.01) | |
| *A61F 2/06* | (2013.01) | |
| *A61F 2/88* | (2006.01) | |
| *A61F 2/90* | (2013.01) | |
| *A61B 17/00* | (2006.01) | |

(52) U.S. Cl.
CPC ........ *A61B 17/12163* (2013.01); *A61B 90/39* (2016.02); *A61F 2/07* (2013.01); *A61B 2017/00004* (2013.01); *A61B 2017/1205* (2013.01); *A61B 2090/3966* (2016.02); *A61F 2/88* (2013.01); *A61F 2/90* (2013.01); *A61F 2002/065* (2013.01); *A61F 2002/077* (2013.01)

(58) Field of Classification Search
CPC ...... A61B 17/12163; A61B 2017/1205; A61B 17/12022; A61F 2/07; A61F 2/958; A61M 29/00

See application file for complete search history.

(56) References Cited

U.S. PATENT DOCUMENTS

| | | |
|---|---|---|
| 4,108,173 A | 8/1978 | Silvenko |
| 4,301,803 A | 11/1981 | Handa et al. |
| 4,341,218 A | 7/1982 | U |
| 4,346,712 A | 8/1982 | Handa et al. |
| 4,553,545 A | 11/1985 | Maass et al. |
| 4,577,631 A | 3/1986 | Kreamer |
| 4,638,803 A | 1/1987 | Rand |
| 4,641,653 A | 2/1987 | Rockey |
| 4,728,328 A | 3/1988 | Hughes et al. |
| 4,944,745 A | 7/1990 | Sogard et al. |
| 4,994,069 A * | 2/1991 | Ritchart ........... A61B 17/12022 604/104 |
| 5,078,726 A | 1/1992 | Kreamer |
| 5,104,404 A | 4/1992 | Wolff |
| 5,133,731 A | 7/1992 | Butler et al. |
| 5,151,105 A | 9/1992 | Kwan-Gett |
| 5,156,620 A | 10/1992 | Pigott |
| 5,163,953 A | 11/1992 | Vince |
| 5,192,301 A | 3/1993 | Kamiya et al. |
| 5,226,911 A | 7/1993 | Chee et al. |
| 5,282,824 A | 2/1994 | Gianturco |
| 5,308,356 A | 5/1994 | Blackshear, Jr. et al. |
| 5,312,415 A | 5/1994 | Palermo |
| 5,330,528 A | 7/1994 | Lazim |
| 5,334,217 A | 8/1994 | Das |
| 5,360,443 A | 11/1994 | Barone et al. |
| 5,395,333 A | 3/1995 | Brill |
| 5,411,550 A | 5/1995 | Herweck et al. |
| 5,478,309 A | 12/1995 | Sweezer et al. |
| 5,530,528 A | 6/1996 | Houki et al. |
| 5,534,024 A | 7/1996 | Rogers et al. |
| 5,540,711 A | 7/1996 | Kieturakis et al. |
| 5,558,642 A | 9/1996 | Schweich, Jr. et al. |
| 5,575,317 A | 11/1996 | Martin |
| 5,578,071 A | 11/1996 | Parodi |
| 5,582,619 A | 12/1996 | Ken |
| 5,591,195 A | 1/1997 | Taheri et al. |
| 5,593,442 A | 1/1997 | Klein |
| 5,613,981 A | 3/1997 | Boyle et al. |
| 5,628,783 A | 5/1997 | Quiachon et al. |
| 5,665,117 A | 9/1997 | Rhodes |
| 5,667,767 A | 9/1997 | Greff et al. |
| 5,693,088 A | 12/1997 | Lazarus |
| 5,702,361 A | 12/1997 | Evans et al. |
| 5,713,917 A | 2/1998 | Leonhardt et al. |
| 5,725,568 A | 3/1998 | Hastings |
| 5,728,131 A | 3/1998 | Frantzen et al. |
| 5,749,894 A | 5/1998 | Engelson |
| 5,752,974 A | 5/1998 | Rhee et al. |
| 5,766,160 A | 6/1998 | Samson et al. |
| 5,769,882 A | 6/1998 | Fogarty et al. |
| 5,785,679 A | 7/1998 | Abolfathi et al. |
| 5,795,331 A | 8/1998 | Cragg et al. |
| 5,800,526 A | 9/1998 | Anderson et al. |
| 5,823,198 A | 10/1998 | Jones et al. |
| 5,824,037 A | 10/1998 | Fogarty et al. |
| 5,824,040 A | 10/1998 | Cox et al. |
| 5,830,230 A | 11/1998 | Berryman et al. |
| 5,843,160 A | 12/1998 | Rhodes |
| 5,861,003 A | 1/1999 | Latson et al. |
| 5,876,448 A | 3/1999 | Thompson et al. |
| 5,916,235 A | 6/1999 | Guglielmi |
| 5,925,059 A | 7/1999 | Palermo et al. |
| 5,928,260 A | 7/1999 | Chin et al. |
| 5,935,145 A | 8/1999 | Villar et al. |
| 5,944,733 A | 8/1999 | Engelson |
| 5,951,599 A | 9/1999 | McCrory |
| 5,980,514 A | 11/1999 | Kupiecki et al. |
| 5,984,963 A | 11/1999 | Ryan et al. |
| 5,994,750 A | 11/1999 | Yagi |
| 6,015,424 A | 1/2000 | Rosenbluth et al. |
| 6,015,431 A | 1/2000 | Thornton et al. |
| 6,024,754 A | 2/2000 | Engelson |
| 6,059,823 A | 5/2000 | Holman et al. |
| 6,063,121 A | 5/2000 | Xavier et al. |
| 6,066,149 A | 5/2000 | Samson et al. |
| 6,080,194 A | 6/2000 | Pachence et al. |
| 6,093,199 A | 7/2000 | Brown et al. |
| 6,096,021 A | 8/2000 | Helm et al. |
| 6,102,940 A | 8/2000 | Robichon et al. |
| 6,110,198 A | 8/2000 | Fogarty et al. |
| 6,113,629 A | 9/2000 | Ken |
| 6,136,015 A | 10/2000 | Kurz et al. |
| 6,139,520 A | 10/2000 | McCrory et al. |
| 6,146,373 A | 11/2000 | Cragg et al. |
| 6,149,664 A | 11/2000 | Kurz |
| 6,152,956 A | 11/2000 | Pierce |
| 6,165,193 A | 12/2000 | Greene, Jr. et al. |
| 6,165,194 A | 12/2000 | Denardo |
| 6,168,592 B1 | 1/2001 | Kupiecki et al. |
| 6,190,402 B1 | 2/2001 | Horton et al. |
| 6,193,745 B1 | 2/2001 | Fogarty et al. |
| 6,196,230 B1 | 3/2001 | Hall et al. |
| 6,203,550 B1 | 3/2001 | Olson |
| 6,203,779 B1 | 3/2001 | Ricci et al. |
| 6,214,036 B1 | 4/2001 | Letendre et al. |
| 6,231,562 B1 | 5/2001 | Khosravi et al. |
| 6,238,403 B1 | 5/2001 | Greene, Jr. et al. |
| 6,248,122 B1 | 6/2001 | Klumb et al. |
| 6,261,305 B1 | 7/2001 | Marotta et al. |
| 6,273,909 B1 | 8/2001 | Kugler et al. |
| 6,273,917 B1 | 8/2001 | Inoue |
| 6,283,991 B1 | 9/2001 | Cox et al. |
| 6,287,315 B1 | 9/2001 | Wijeratne et al. |
| 6,287,335 B1 | 9/2001 | Drasler et al. |
| 6,290,731 B1 | 9/2001 | Solovay et al. |
| 6,293,960 B1 | 9/2001 | Ken |
| 6,296,603 B1 | 10/2001 | Turnlund et al. |
| 6,296,604 B1 | 10/2001 | Garibaldi et al. |
| 6,299,597 B1 | 10/2001 | Buscemi |
| 6,299,619 B1 | 10/2001 | Greene, Jr. et al. |
| 6,312,421 B1 | 11/2001 | Boock |
| 6,312,462 B1 | 11/2001 | McDermott et al. |
| 6,312,463 B1 | 11/2001 | Rourke et al. |
| 6,315,709 B1 | 11/2001 | Garibaldi et al. |
| 6,319,276 B1 | 11/2001 | Holman et al. |
| 6,325,819 B1 | 12/2001 | Pavcnik et al. |

(56) References Cited

U.S. PATENT DOCUMENTS

| | | | |
|---|---|---|---|
| 6,331,184 B1 | 12/2001 | Abrams | |
| 6,334,869 B1 | 1/2002 | Leonhardt et al. | |
| 6,344,041 B1 | 2/2002 | Kupiecki et al. | |
| 6,344,048 B1 | 2/2002 | Chin et al. | |
| 6,344,056 B1 | 2/2002 | Dehdashtian | |
| 6,350,270 B1 | 2/2002 | Roue | |
| 6,358,556 B1 | 3/2002 | Ding et al. | |
| 6,361,556 B1 | 3/2002 | Chuter | |
| 6,364,823 B1 | 4/2002 | Garibaldi et al. | |
| 6,375,668 B1 | 4/2002 | Gifford et al. | |
| 6,375,669 B1 | 4/2002 | Rosenbluth et al. | |
| 6,379,329 B1 | 4/2002 | Naglreiter et al. | |
| 6,383,174 B1 | 5/2002 | Eder | |
| 6,395,019 B2 | 5/2002 | Chobotov | |
| 6,409,757 B1 | 6/2002 | Trout, III et al. | |
| 6,458,119 B1 | 10/2002 | Berenstein et al. | |
| 6,463,317 B1 | 10/2002 | Kucharczyk et al. | |
| 6,485,510 B1 | 11/2002 | Camrud et al. | |
| 6,494,889 B1 | 12/2002 | Fleischman et al. | |
| 6,506,204 B2 | 1/2003 | Mazzocchi | |
| 6,511,468 B1 | 1/2003 | Cragg et al. | |
| 6,521,244 B1 | 2/2003 | Kanesaka | |
| 6,527,739 B1 | 3/2003 | Bigus et al. | |
| 6,544,219 B2 * | 4/2003 | Happ .................. | A61F 2/958 604/104 |
| 6,544,276 B1 | 4/2003 | Azizi | |
| 6,551,280 B1 | 4/2003 | Knighton et al. | |
| 6,551,303 B1 | 4/2003 | Van Tassel et al. | |
| 6,558,367 B1 | 5/2003 | Cragg et al. | |
| 6,565,602 B2 | 5/2003 | Rolando et al. | |
| 6,585,756 B1 | 7/2003 | Strecker | |
| 6,585,760 B1 | 7/2003 | Fogarty | |
| 6,589,265 B1 | 7/2003 | Palmer et al. | |
| 6,592,614 B2 | 7/2003 | Lenker et al. | |
| 6,613,037 B2 | 9/2003 | Khosravi et al. | |
| 6,613,074 B1 | 9/2003 | Mitelberg et al. | |
| 6,616,684 B1 | 9/2003 | Vidlund et al. | |
| 6,626,928 B1 | 9/2003 | Raymond et al. | |
| 6,626,938 B1 | 9/2003 | Butaric et al. | |
| 6,629,947 B1 | 10/2003 | Sahatjian et al. | |
| 6,645,167 B1 | 11/2003 | Whalen, II et al. | |
| 6,656,214 B1 | 12/2003 | Fogarty et al. | |
| 6,663,607 B2 | 12/2003 | Slaikeu et al. | |
| 6,663,667 B2 | 12/2003 | Dehdashtian et al. | |
| 6,692,510 B2 | 2/2004 | West | |
| 6,695,876 B1 | 2/2004 | Marotta et al. | |
| 6,712,826 B2 | 3/2004 | Lui | |
| 6,723,108 B1 | 4/2004 | Jones et al. | |
| 6,729,356 B1 | 5/2004 | Baker et al. | |
| 6,730,119 B1 | 5/2004 | Smalling | |
| 6,764,510 B2 | 7/2004 | Vidlund et al. | |
| 6,827,735 B2 | 12/2004 | Greenberg | |
| 6,843,803 B2 | 1/2005 | Ryan et al. | |
| 6,852,097 B1 | 2/2005 | Fulton, III | |
| 6,921,410 B2 | 7/2005 | Porter | |
| 7,070,609 B2 | 7/2006 | West | |
| 7,070,616 B2 | 7/2006 | Majercak et al. | |
| 7,081,129 B2 | 7/2006 | Chobotov | |
| 7,101,396 B2 | 9/2006 | Artof et al. | |
| 7,128,736 B1 | 10/2006 | Abrams et al. | |
| 7,147,660 B2 | 12/2006 | Chobotov et al. | |
| 7,147,661 B2 | 12/2006 | Chobotov et al. | |
| 7,530,988 B2 | 5/2009 | Evans et al. | |
| 7,615,071 B2 | 11/2009 | Chobotov | |
| 7,708,771 B2 | 5/2010 | Chuter et al. | |
| 8,231,665 B2 | 7/2012 | Kim et al. | |
| 8,231,666 B2 | 7/2012 | Kim et al. | |
| 8,262,686 B2 | 9/2012 | Fogarty et al. | |
| 8,361,136 B2 | 1/2013 | Chobotov | |
| 8,535,367 B2 | 9/2013 | Kim et al. | |
| 8,562,662 B2 | 10/2013 | Kim et al. | |
| 8,647,377 B2 | 2/2014 | Kim et al. | |
| 8,801,769 B2 | 8/2014 | Chobotov | |
| 8,936,633 B2 | 1/2015 | Kim et al. | |
| 9,295,569 B2 | 3/2016 | Kim et al. | |
| 9,561,037 B2 | 2/2017 | Fogarty et al. | |
| 9,561,096 B2 | 2/2017 | Kim et al. | |
| 9,561,097 B1 | 2/2017 | Kim et al. | |
| 9,615,912 B2 | 4/2017 | Fogarty et al. | |
| 9,629,636 B2 | 4/2017 | Fogarty et al. | |
| 2001/0020184 A1 | 9/2001 | Dehdashtian et al. | |
| 2001/0044621 A1 | 11/2001 | Klumb et al. | |
| 2001/0047202 A1 | 11/2001 | Slaikeu et al. | |
| 2002/0019665 A1 | 2/2002 | Dehdashtian et al. | |
| 2002/0026217 A1 | 2/2002 | Baker et al. | |
| 2002/0045848 A1 | 4/2002 | Jaafar et al. | |
| 2002/0052643 A1 | 5/2002 | Wholey et al. | |
| 2002/0058986 A1 | 5/2002 | Landau et al. | |
| 2002/0065542 A1 | 5/2002 | Lax et al. | |
| 2002/0077693 A1 | 6/2002 | Barclay et al. | |
| 2002/0082638 A1 | 6/2002 | Porter et al. | |
| 2002/0082682 A1 | 6/2002 | Barclay et al. | |
| 2002/0099441 A1 | 7/2002 | Dehdashtian | |
| 2002/0107565 A1 | 8/2002 | Greenhalgh | |
| 2002/0151957 A1 | 10/2002 | Kerr | |
| 2002/0169497 A1 | 11/2002 | Wholey et al. | |
| 2002/0183841 A1 | 12/2002 | Cohn et al. | |
| 2002/0193821 A1 | 12/2002 | Trout | |
| 2003/0004531 A1 | 1/2003 | Jones et al. | |
| 2003/0014075 A1 | 1/2003 | Rosenbluth et al. | |
| 2003/0028209 A1 | 2/2003 | Teoh et al. | |
| 2003/0051735 A1 | 3/2003 | Pavcnik et al. | |
| 2003/0074017 A1 | 4/2003 | Shah | |
| 2003/0130724 A1 | 7/2003 | DePalma et al. | |
| 2003/0171805 A1 | 9/2003 | Berg et al. | |
| 2003/0195607 A1 | 10/2003 | Trout et al. | |
| 2003/0204246 A1 | 10/2003 | Chu et al. | |
| 2003/0216802 A1 | 11/2003 | Chobotov | |
| 2003/0220666 A1 | 11/2003 | Mirigian et al. | |
| 2003/0220667 A1 | 11/2003 | van der Burg et al. | |
| 2003/0229286 A1 | 12/2003 | Lenker | |
| 2004/0044358 A1 | 3/2004 | Khosravi et al. | |
| 2004/0044361 A1 | 3/2004 | Frazier et al. | |
| 2004/0073190 A1 | 4/2004 | Deem et al. | |
| 2004/0073288 A1 | 4/2004 | Kerr | |
| 2004/0098027 A1 | 5/2004 | Teoh et al. | |
| 2004/0116997 A1 | 6/2004 | Taylor et al. | |
| 2004/0186556 A1 | 9/2004 | Hogendijk et al. | |
| 2004/0210249 A1 | 10/2004 | Fogarty et al. | |
| 2004/0254625 A1 | 12/2004 | Stephens et al. | |
| 2006/0292206 A1 | 12/2006 | Kim et al. | |
| 2007/0050008 A1 | 3/2007 | Kim et al. | |
| 2007/0055355 A1 | 3/2007 | Kim et al. | |
| 2007/0061005 A1 | 3/2007 | Kim et al. | |
| 2008/0275536 A1 | 11/2008 | Zarins et al. | |
| 2012/0179192 A1 | 7/2012 | Fogarty et al. | |
| 2012/0265287 A1 | 10/2012 | Sharma et al. | |
| 2012/0330343 A1 | 12/2012 | Kim et al. | |
| 2013/0060320 A1 | 3/2013 | Fogarty et al. | |
| 2014/0081374 A1 | 3/2014 | Kim et al. | |
| 2014/0088690 A1 | 3/2014 | Fogarty et al. | |
| 2014/0142685 A1 | 5/2014 | Kim et al. | |
| 2017/0020653 A1 | 1/2017 | Kim et al. | |
| 2017/0020654 A1 | 1/2017 | Fogarty et al. | |
| 2017/0086853 A1 | 3/2017 | Fogarty et al. | |

FOREIGN PATENT DOCUMENTS

| | | |
|---|---|---|
| WO | WO 1999/016384 | 4/1999 |
| WO | WO 1999/043273 | 9/1999 |
| WO | WO 1999/065418 | 12/1999 |
| WO | WO 2000/069367 | 11/2000 |
| WO | WO 2001/006950 | 2/2001 |
| WO | WO 2001/028434 | 4/2001 |
| WO | WO 2001/093920 | 12/2001 |
| WO | WO 2002/102282 | 12/2002 |
| WO | WO 2004/045393 | 6/2004 |

OTHER PUBLICATIONS

Pyo et al, "Targeted Gene Disruption of Matrix Metalloproteinase-9 (Gelatinase B) Suppresses Development of Experimental Abdomi-

(56) References Cited

OTHER PUBLICATIONS nal Aortic Aneurysms," *J. Clinical Investigation,* 105(11):1641-1649, 2000.

Tambiah et al, "Provocation of Experimental Aortic Inflammation Mediators and Chlamydia Pneumoniae," *Brit. J. Surgery,* 88(7):935-940, 2001.

Villareal et al, "Early Results Using Bare Metal Stents With or Without Coil Embolization for AAA Exclusion," *Journal of endovascular therapy : an official journal of the International Society of Endovascular Speciatists,* 8 pages, 2001.

Walton, et al, "Inhibition of Prostoglandin E2 Synthesis in Abdominal Aortic Aneurysms," *Circulation,* pp. 48-54, Jul. 6, 1999.

Xu et al, "Sp 1 Increases Expression of Cyclooxygenase-2 in Hypoxic Vascular Endothelium," *J. Biological Chemistry,* 275(32):24583-24589, 2000.

\* cited by examiner

NOT INVENTION

NOT INVENTION

EMBOLIZATION DEVICE AND A METHOD OF USING THE SAME

CROSS-REFERENCE TO RELATED APPLICATION

This application is a continuation of U.S. application Ser. No. 14/657,888, filed Mar. 13, 2015, which is a continuation of U.S. application Ser. No. 14/058,986, filed Oct. 21, 2013, (now U.S. Pat. No. 9,005,235 issued Apr. 14, 2015), which is a continuation of U.S. application Ser. No. 13/569,348, filed Aug. 8, 2012, (now U.S. Pat. No. 8,562,636 issued Oct. 22, 2013), which is a divisional of U.S. application Ser. No. 12/340,483, filed Dec. 19, 2008, (now U.S. Pat. No. 8,262,686 issued Sep. 11, 2012), which is a continuation of U.S. application Ser. No. 10/293,139, filed Nov. 12, 2002, (now U.S. Pat. No. 7,481,821 issued Jan. 27, 2009), each of which are incorporated by reference herein in their entireties.

BACKGROUND OF THE INVENTION

1. Field of the Invention

The present invention relates generally to a device for filling and/or stabilizing the void within an anatomical organ of the body, particularly within the vasculature, and methods for making and using the device.

2. Description of the Related Art

An aneurysm is an abnormal dilatation of a biological vessel. Aneurysms can alter flow through the affected vessel and often decrease the strength of the vessel wall, thereby increasing the vessel's risk of rupturing at the point of dilation or weakening. FIG. 1 illustrates an abdominal aorta 2 with a sacular aneurysm 4 having, an aneurysm wall 6. FIG. 2 illustrates the abdominal aorta 2 with a vascular prosthesis 8 implanted to treat the aneurysm 4, a common aneurysm therapy. Vascular grafts and stent-grafts (e.g., ANEURX® Stent Graft System from Medtronic AVE, Inc., Santa Rosa, Calif.) are examples of vascular prostheses used to treat aneurysms by reconstructing the damaged vessel.

With the prosthesis 8 implanted, an aneurysm sac 10 is defined by the volume between the prosthesis 8 and the aneurysm wall 6. The sac 10 is often filled, partially or completely, with thrombi 12. The thrombi 12 can be partially removed prior to deploying the prosthesis 8. Whether the thrombi 12 are removed, gaps exist between the remaining thrombi 12 or the aneurysm wall 6 and the prosthesis 8, and even when thrombus is present, it can be soft and non-structural. The prosthesis 8 can dislodge or migrate due to the poor fit caused by these gaps and shrinkage of the sac 10 that occurs after the implantation of the prosthesis 8, either acutely due to sizing issues, or over time due to reformation of the sac 10. To reduce the risk of prosthesis dislodgement and migration, the sac 10 can be filled to stabilize the anatomy adjacent to the prosthesis 8 resulting in better efficacy of the prosthetic treatment.

A sac filler, or stabilizer, can be introduced to the sac 10 by trans-graft, trans-collateral, trans-sac, or endoluminal procedures. The trans-graft procedure introduces the sac filler through an opening in the prosthesis 8, as shown by arrows 12. The trans-collateral procedure, shown by arrows 16, introduces the sac filler through a collateral vessel 18 under fluoroscopic guidance that is in direct communication with the sac 10. The trans-sac procedure, often performed laparoscopically, introduces the sac filler through a puncture in the wall 6 of the aneurysm, as shown by arrows 20. The endoluminal procedure introduces the sac filler through the vessel that has the aneurysm 4, as shown by arrows 22, but within the space between the prosthesis and the vessel wall. The trans-graft, trans-collateral and endoluminal procedures are often performed as minimally invasive, entirely endovascular procedures.

It is desirable for a stabilizing element or sac filler to conform to the available space within the sac 10 by operation of the geometry of the device (e.g., by nesting or coiling) and/or by any coatings or materials utilized to promote fusing or other coagulative effect.

U.S. Pat. No. 6,146,373 to Cragg et al. discloses a catheter system and method for injecting a liquid embolic composition and a solidification agent directly into a sac. Cragg et al. teach the use of organic solvents such as DIMSO, ethanol and others injected directly in the aneurysm. Cragg et al. teach that these solvents can be toxic to tissue and may cause vascular spasms. Using liquid-solidifying agents in vessels also carries a high risk that the agents will flow downstream creating emboli or flow into collateral vessels (e.g., lumbar arteries), which may lead to paralysis or other adverse events.

U.S. Pat. No. 4,994,069 to Ritchart et al., U.S. Pat. No. 5,133,731 to Butler et al., U.S. Pat. No. 5,226,911 to Chee et al. and U.S. Pat. No. 5,312,415 to Palermo disclose examples of thrombogenic microcoils, common aneurysm treatments. The microcoil must be tightly packed into the aneurysm to minimize shifting of the microcoils. Shifting of the microcoil can lead to recanalization of the aneurysm. Another disadvantage of microcoils is that they are not easily retrievable. If a coil migrates out of the aneurysm, a second procedure to retrieve the coil and move the coil back into place, or replace the coil, might be necessary.

U.S. Pat. Nos. 6,238,403 and 6,299,619, both to Greene, Jr. et al disclose an embolic device with expansible elements and methods for embolizing a target vascular site with the device. The device taught by Greene Jr. includes a plurality of highly-expansible elements disposed at spaced intervals along a filamentous carrier. The expansion of the device after deployment reduces the volumetric precision with which the sac can be filled. If the volume of the expanded device is too large, the device can press against the inner side of weakened aneurysm wall and outer side of prosthesis, altering flow within the prosthesis and increasing the risk of rupture of the aneurysm. If the volume of the expanded device is too small, the prosthesis can still alter its position and dislodge or migrate.

There is thus a need for a device and method that can precisely occlude a known sac volume with minimal displacement sac 10 while of the device over time. There is also a need for a device that can be deployed to the simultaneously minimizing toxicity, embolism risk, and other disadvantages previously associated with existing aneurysm sac fillers.

BRIEF SUMMARY OF THE INVENTION

One embodiment of the disclosed device is a vascular embolization device having a flexible leader connected to at least one non-expandable, space-occupying element. The elements can be made, for example, from collagen and/or a polymer such as polypropylene. The device can also have a radiopaque agent fixed to or integrated with the device. Furthermore, the device can be coated or infused with a therapeutic and or diagnostic agent.

Another embodiment of the disclosed device is a vascular embolization device having a leader made from a flexible material and a space-occupying element connected to the leader. The element has a first component secured to a second component. The element can also be slidably connected to the leader, for example, by a ferrule.

Yet another embodiment of the disclosed device is a vascular embolization device having one or more cylindrical space-occupying elements connected by flexible helical segments. When fully extended, the element has a cross-sectional width to cross-sectional height ratio of equal to or greater than about 1.5:1. The cross-sectional width-to-height ratio can also be equal to or greater than 4:1.

A further embodiment of the disclosed device is a vascular embolization device having a first space-occupying element having a first male interference-fit piece, and a second space-occupying element having a first female interference-fit piece. The first male interference-fit piece and the first female interference-fit piece attach to impede removal of the first male interference-fit piece from the first female interference-fit piece.

Yet another embodiment of the disclosed device is a vascular embolization device. The device has a first space-occupying element comprising a body and a first female interference-fit piece. The device also has a second space-occupying element comprising a body and a second female interference-fit piece. Furthermore, the device has a leader comprising a first male interference-fit piece on a first end and a second male interference-fit piece on a second end. The first male interference-fit piece attaches to the first female interference-fit piece attach and the second male interference-fit piece attaches to the second female interference-fit piece.

A method is also disclosed for placing a space-occupying device or a plurality of space-occupying devices, such as the embolization devices disclosed herein, within a void. For example, a catheter having a distal exit is placed at a vascular site. A vascular embolization device is then passed through the catheter and the distal exit and deployed into the vascular site. The device has a flexible leader and at least one non-expandable, space-occupying elements connected to the leader. The method can include selecting a device or devices having the proper volume so that the device(s) is large enough to substantially fill the void, such as an aneurysmal sac within the vasculature, yet small enough to prevent substantial alteration of the natural fluid flow through an adjacent element, for example a vascular prosthesis implanted at or near the vascular site. Furthermore, the method of the present invention may provide for the removal of material within the void, such as the removal of thrombus from the aneurysmal sac and treatment with therapeutic agents prior to, or in conjunction with, the placement of the space-occupying elements.

BRIEF DESCRIPTION OF THE DRAWINGS

FIG. 3b illustrates a portion of the embolization device of FIG. 3a.

DETAILED DESCRIPTION

Figure 2:
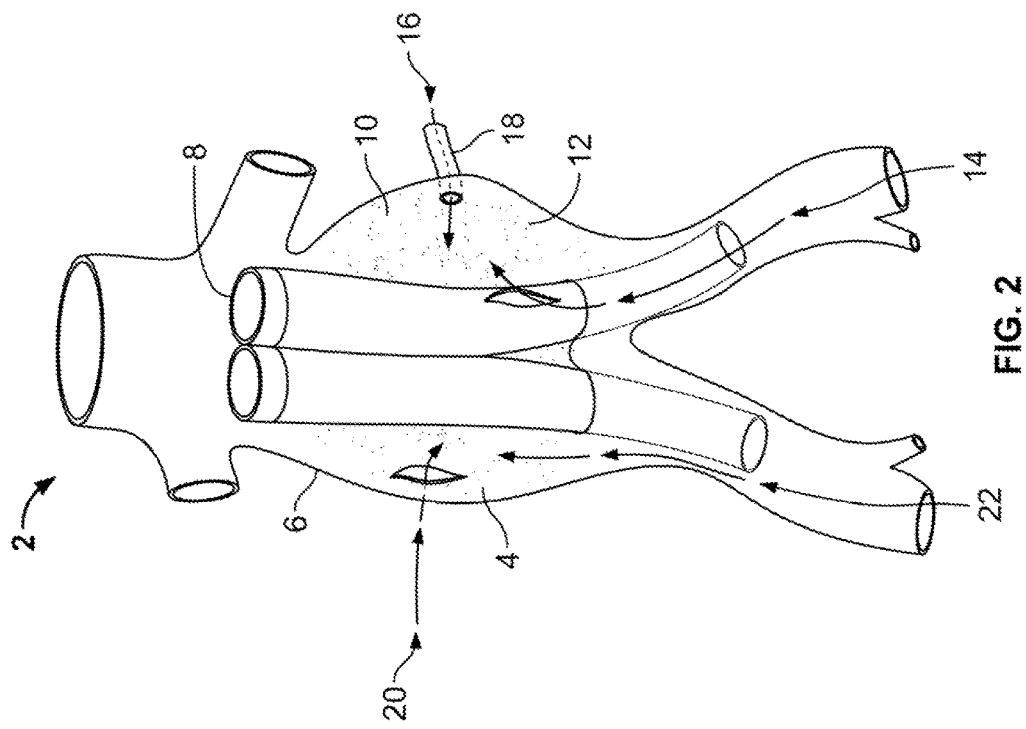
FIG. 2 not the invention, illustrates a vascular prosthesis implant within at aneurysm and procedures for filling the aneurysm sac.
Figure 1:
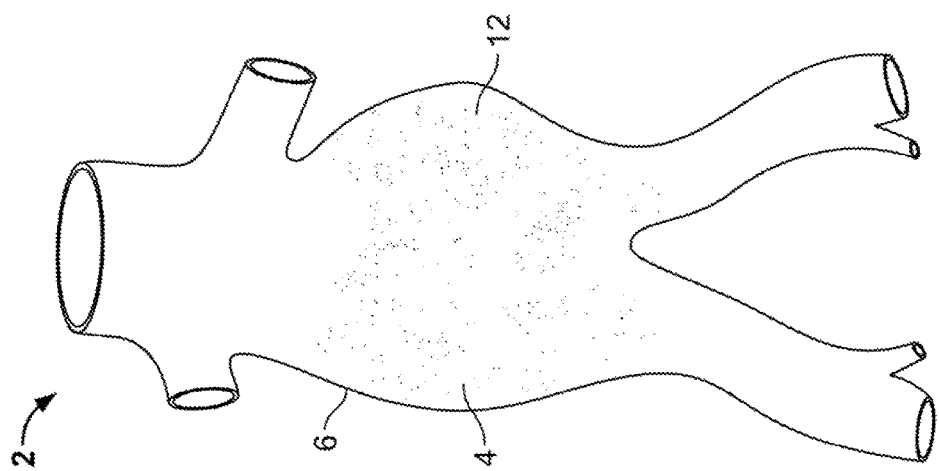
FIG. 1 not the invention, illustrates an aneurysm.
Figure 3A:
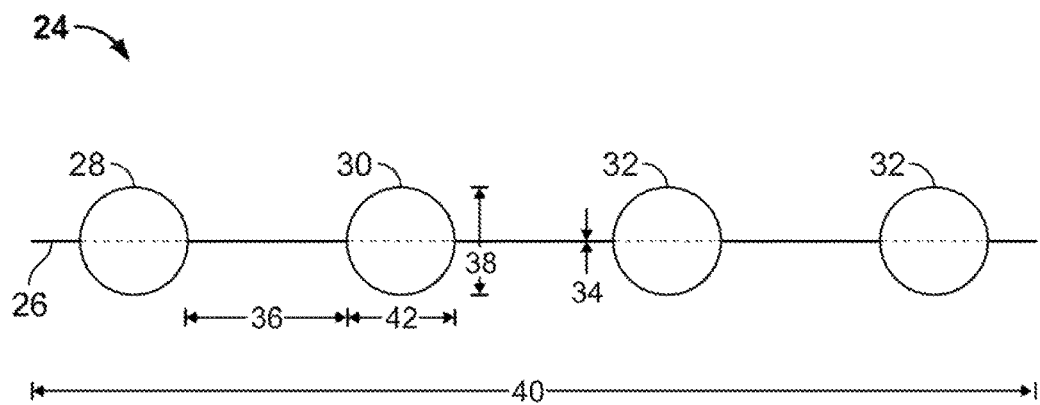
FIG. 3a illustrates an embodiment of the embolization device.
Figure 3B:
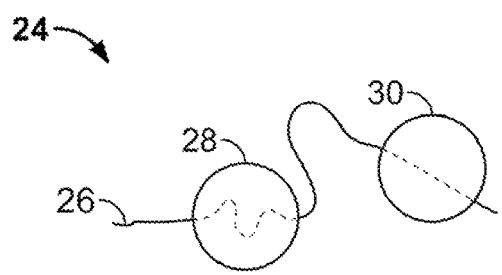

FIG. 3a illustrates an embodiment of a vascular embolization or occlusion device 24 having a flexible leader 26 that can be connected to a first non-expandable space-occupying element 28 and a second non-expandable space-occupying element 30. Additional non-expandable space-occupying elements 32 can also be connected to the leader 26 and provided in various lengths, depending on the typical volume of the sac 10 to be filled. The leader 26 can pass through the elements 28, 30 and 32. The leader 26 can be fixed to the elements 28, 30 and 32, or the elements 28, 30 and 32 can slide freely over the leader 26. As illustrated in FIG. 3b, the leader 26, even if secured within an element 28, 30, or 32, can flex and bend within each element 28, 30 or 32, or between the elements 28, 30 and 32.

The leader 26 can be a suture, preformed resilient structure, poppet, wire, fiber, monofilament, rail, or a woven thread or other combination thereof. The leader 26 can be completely separate and discrete from the elements 28, 30 and 32. The leader 26 can be made from polymer, for example polyester (e.g., DACRON® from E. I. du Pont de Nemours and Company, Wilmington, Del.), polypropylene, polytetrafluoroethylene (PTFE), expanded PTFE (ePTFE), nylon, extruded collagen, silicone and combinations thereof. The leader 26 can have a leader diameter 34 from about 0.050 mm (0.0020 in.) to about 1.3 mm (0.050 in.), more narrowly from about 0.2 mm (0.006 in.) to about 0.25 mm (0.010 in.). A leader span 36 between the elements 28 and 30 can be from about 0 to about 2 times an element outer diameter 38, more narrowly from about 0.5 to about 1 time the element outer diameter 38. A total device length 40 from one end of the device 24 to the other can be any length desired, for example about 30 cm (1 ft.).

The elements 28, 30 and 32 can be spherical, cylindrical, or an approximation thereof. The elements 28, 30 and 32 can be made from any of the materials disclosed above for the leader 26 as well as collagen, glass, polylactic acid (PLA), poly(lactic-co-glycolic acid) (PLGA), polyglycolic acid (PGA), other bioabsorbable material, polyurethane, polyethylene, or metal, for example stainless steel, titanium or nitinol. The element outer diameter 38 can be more than about 0.1 mm (0.005 in.) of the leader diameter 34. The element outer diameter 38 can be larger than about 0.25 mm (0.010 in.) less than an inner diameter of a catheter through which the device 24 is deployed. The element outer diameter 38 can also be larger than about 2.0 mm (0.079 in.), more narrowly lamer than about 2.7 mm (0.11 in.). An element length 42 can be in the aforementioned ranges for the element outer diameter 38.

A device volume can be determined by calculating the total volume of the elements 28, 30 and 32 added to the total volume of the leaders 26. If the leader 26 or the elements 28, 30 and 32 are made from bioabsorbable materials, the reduction of device volume over time can be accounted for when calculating device volume. The device volume can be from about 20 cc (1.2 in.$^3$) to about 200 cc (12.2 in.$^3$), more narrowly from about 60 cc (3.7 in.$^3$) to about 100 cc (6.1 in.$^3$).

Figure 4:
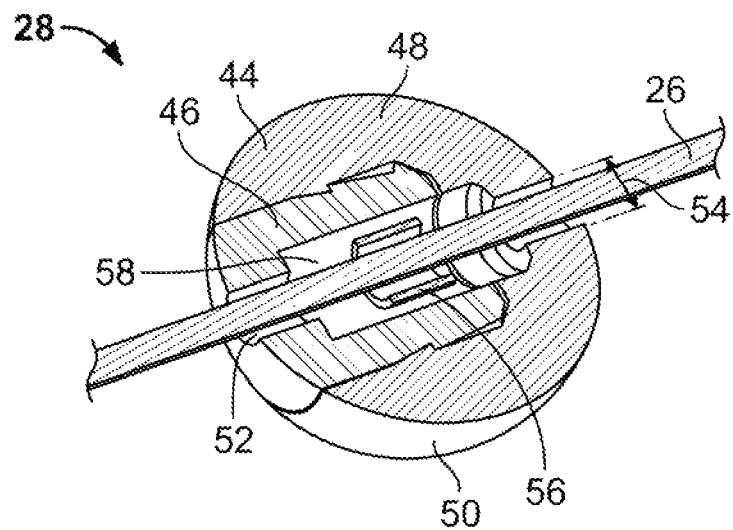
FIG. 4 is a cross-sectional view of an embodiment of the leader and the space-occupying element.
Figure 5:
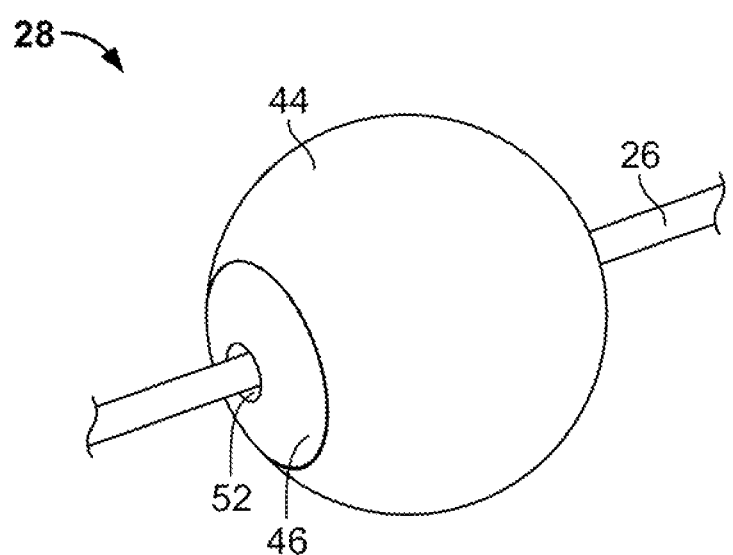
FIG. 5 illustrates an embodiment of the leader and the space-occupying element of FIG. 4.

FIGS. 4 and 5 illustrate an embodiment of the element 28 with the leader 26. The elements 30 and 32 can have embodiments identical to the element 28. The element 28 can be made from a first section 44 and a second section 46. The first section 44 can be secured to the second section 46. The sections 44 and 46 can have a section body 48 and an outer layer 50. The section body 48 can be solid, solid with one or more dimples or channels, or hollow. The outer layer 50 can be a porous membrane or have macroscopic holes or channels that are in communication with the section body 48. The element 28 can have one or more leader channels 52 having leader channel diameters 54 about equal to or greater than the leader diameter 34. The leader channels 52 can be fixed to the leader 26. Alternatively, the leader 26 can have a clearance with the leader channels 52. A ferrule 56 can be fixed to the leader 26. The ferrule 56 can be locked with an interference fit into a ferrule cavity 58.

Figure 6:
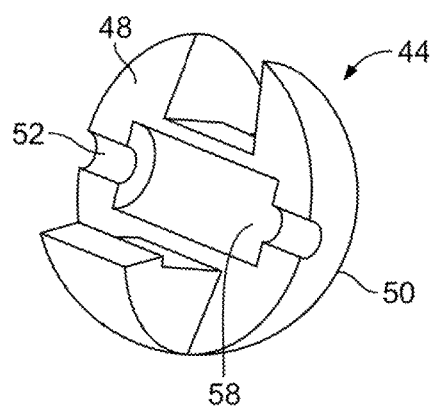
FIG. 6 illustrates an embodiment of the first section of the space-occupying element.
Figure 7:
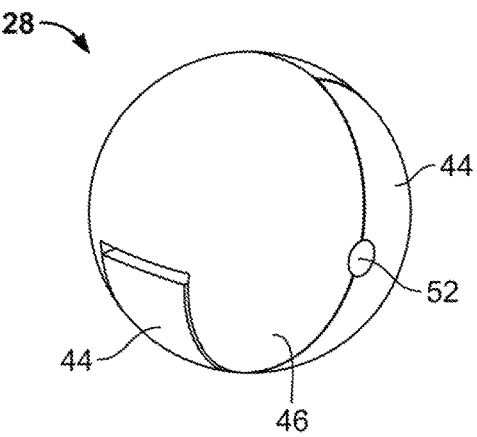
FIG. 7 illustrates an embodiment of the space-occupying element of FIG. 6.
Figure 8:
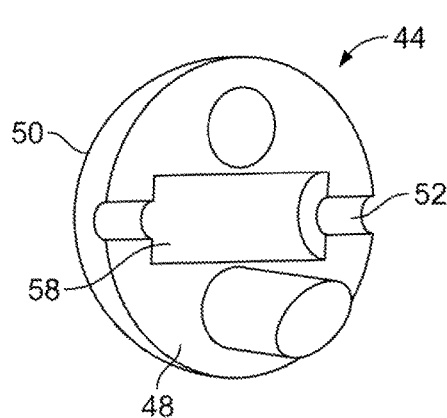
FIG. 8 illustrates an embodiment of the first section of the space-occupying element.
Figure 9:
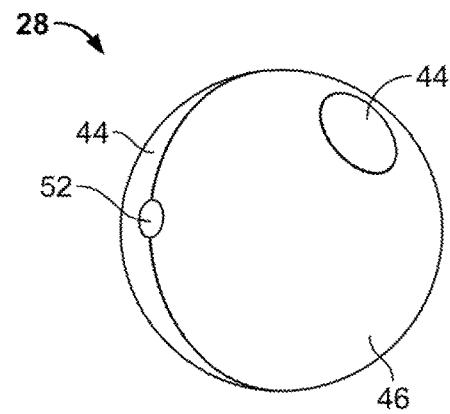
FIG. 9 illustrates an embodiment of the space-occupying element of FIG. 8.

FIGS. 6 and 7 illustrate an embodiment of the first section 44 and the element 28, respectively. FIGS. 8 and 9 illustrate another embodiment of the first section 44 and the element 28, respectively. In the embodiments shown in FIGS. 6-9, the sections 44 and 46 can be identically shaped. In the embodiments in FIGS. 4-7, the sections 44 and 46 can be shaped to fit the opposite section 44 or 46 and form an interference fit, for example a snap lock, with the opposite section 44 or 46. The interference fit minimizes movement of the sections 44 and 46 with respect to each other in any direction. In the embodiments in FIGS. 8 and 9, the sections 44 and 46 can be shaped to fit the opposite section 44 or 46 and form an interference fit that allows movement of the sections 44 and 46 with respect to each other in one translational direction.

Figure 10:
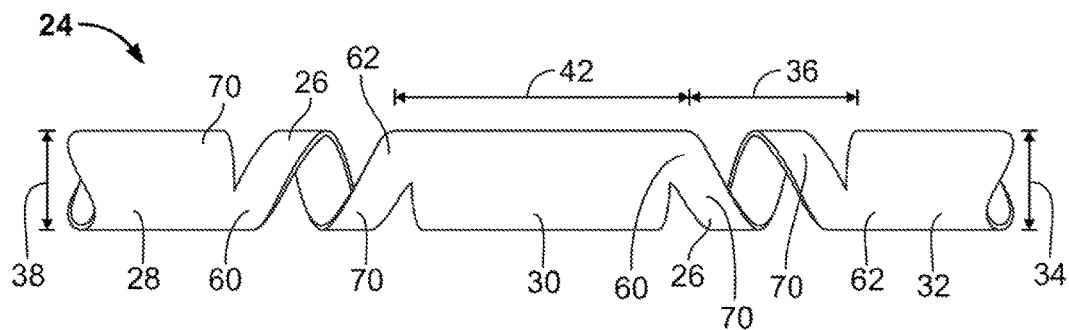
FIGS. 10 and 11 illustrate segments of embodiments of the embolization device.
Figure 11:
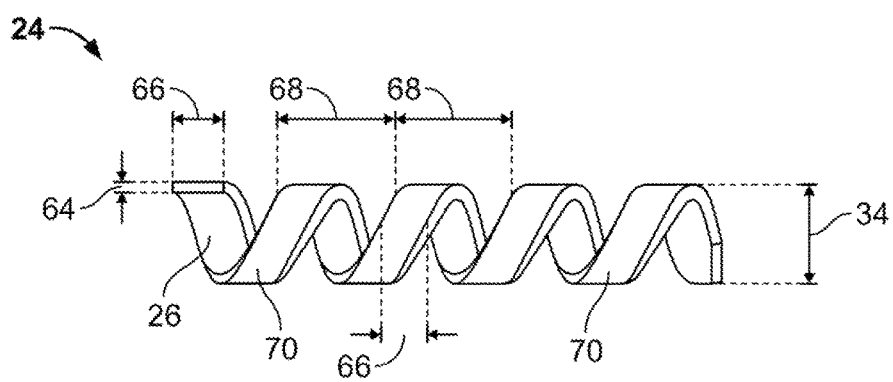

FIG. 10 illustrates a segment of an embodiment of the device 24 with the leaders 26 having first ends 60 and second ends 62 that can be integrated and conjoined segments of the elements 28, 30 and 32. The leaders 26 can be preformed resilient structures formed into helical shapes. The device 24 can be made entirely from the leader 26 and without elements 28, 30 and 32, as illustrated in FIG. 11, or each element 28, 30 or 32 can be separated from the adjacent elements 28, 30 and 32 by as few as about 0.5 turns of the leader 26. More narrowly, each element 28, 30 or 32 can be separated from the adjacent elements 28, 30 and 32 by from about 2 turns to about 3 turns of the leader 26. The leaders 26 can have a preformed leader depth 64 from about 0.25 mm (0.0098 in.) to about 2.0 mm (0.079 in.), more narrowly from about 0.5 mm (0.02 in.) to about 1.0 mm (0.039 in.), and a preformed leader width 66 from about 0.5 mm (0.02 in.) to about 4.0 mm (0.16 in.), more narrowly from about 1.0 mm (0.039 in.) to about 2.0 mm (0.079 in.). The leaders 26 can also have wind lengths 68. The wind lengths 68 can be the longitudinal component of the length covered by about 360 degrees of helical turn in the element 28, 30 or 32. The wind lengths 68 can be about 2.0 mm (0.079 in.). The wind lengths 68 can also vary within a single element 28, 30 or 32, and five wind lengths 68 can be about 1.0 cm (0.39 in.).

The device 24 can be structurally reinforced. For example, a structural reinforcement 70 can be integrated onto the surface or encased by the leader 26 and/or the elements 28, 30, and 32. The reinforcement can be a polyester weave, or a coil or spiral element, for example a continuous wire wound within the device 24 such that the reinforcement 70 parallels the coils or helical shapes of the conjoined elements 28, 30 and 32 of the device 24.

Figure 12A:
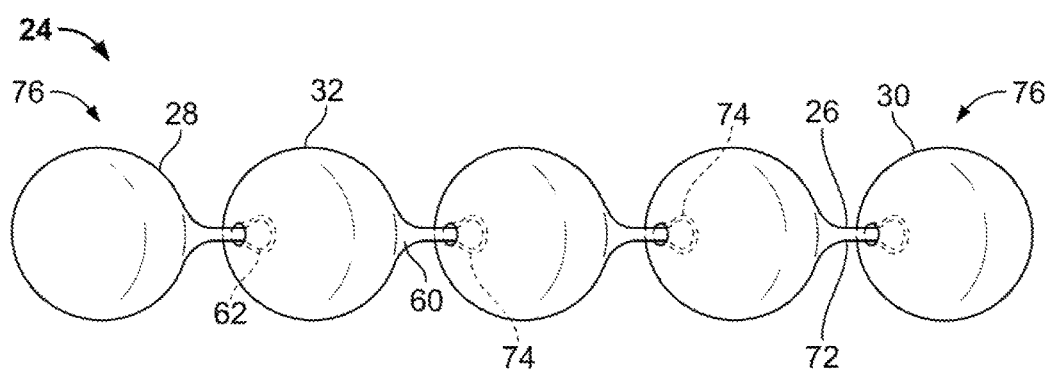
FIGS. 12a-c and 13 illustrate embodiments of the embolization device.
Figure 12B:
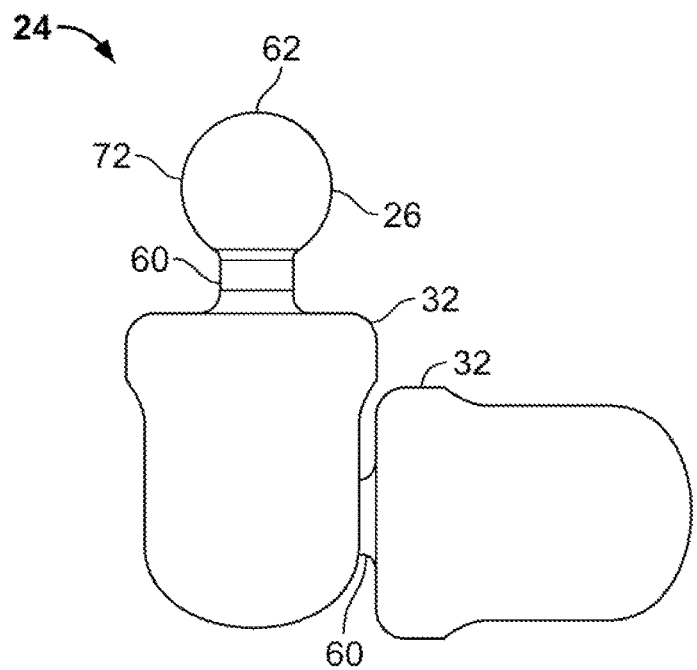
Figure 12C:
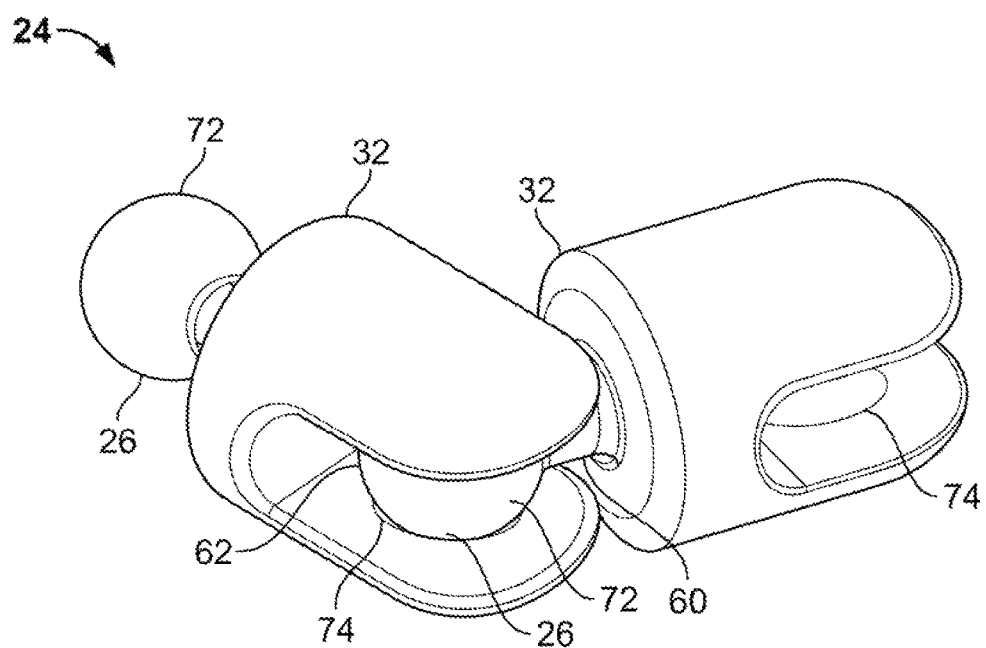

In other embodiments of the device 24 illustrated in FIGS. 12a-c, the leaders 26 can have a male interference-fit piece, for example brads or poppets 72, on a first end 60 of the leaders 26. The second ends 62 of the leaders 26 can be integrated and conjoined with the elements 28, 30 and 32. The elements 28, 30 and 32 can have female interference-fit pieces, for example plugs or sockets 74, integrated into the elements 28, 30 and 32 at the opposite ends of the elements 28, 30 and 32 from the poppets 74. The poppets 72 and sockets 74 can be shaped and sized to attach to each other with a sufficient interference fit to impede removal of the poppets 72 from the sockets 74. The elements 28 and 30 at open ends 76 of the device 24 do not attach to a neighboring element 28, 30 and 32. The elements 28 and 30 at the open ends 76 can lack the poppet 72 or the socket 74 on the open ends 76 of the elements 28 and 30.

Figure 13:
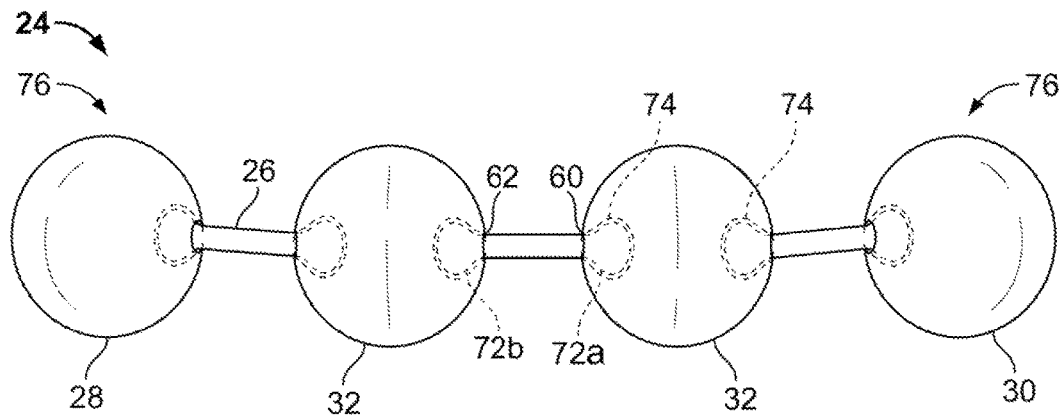

In another embodiment of the device 24 illustrated in FIG. 13, the first end 60 of the leader 26 can have a first male interference-fit piece, for example a first poppet 72a, and the second end 62 of the leader 26 can have a second male interference-fit piece, for example a second poppet 72b. A leader with male interference-fit pieces at two ends can be called a "dogbone". The elements 28, 30 and 32 can have two female interference-fit pieces, for example sockets 74, integrated into opposite ends of each element 28, 30 and 32.

Figure 14:
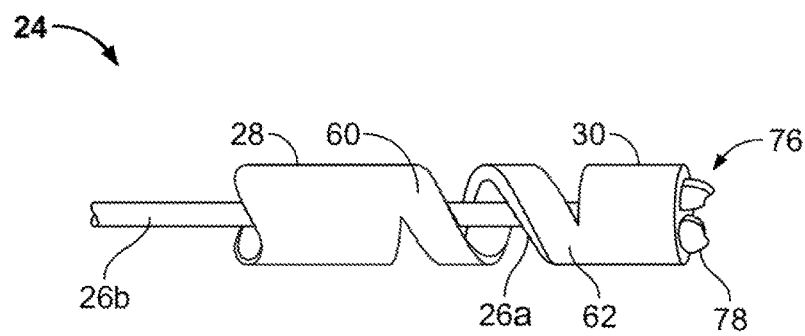
FIG. 14 illustrates a segment of an embodiment of the embolization device.

FIG. 14 illustrates a segment of an embodiment of the device 24 having first leaders 26a with ends 60 and 62 that can be integrated and conjoined segments of the elements 28 and 30 and a second leader 26b that can pass through the first leaders 26a and the elements 28 and 30. The second leader 26b can have an interference fit at one open end 76, for example a knot 78. The second leader 26b can be fixed or slidably attached to the elements 28 and 30.

Radiopaque materials known to one having ordinary skill in the art can be used anywhere in or on the device 24. Examples of radiopaque materials are barium, sulfate, titanium, stainless steel, nickel-titanium alloys (e.g., NiTi), and gold. The ferrule 56 can be made from radiopaque materials. A radiopaque patch or contrast agent can also be integrated into or placed on the leader 26 or the elements 28, 30, and 32. The contrast agent can be permanent or can be adapted to extravagate over time post-implantation. A radiopaque fiber can be wound integrally with the leader 26. The radiopaque element can be present in a quantity sufficient to allow the operator to view deployment of the device 24 upon delivery, but not sufficient to obstruct the visualization of adjacent tissues and structures post-implantation. For example, upon deployment, the operator can visualize the initial placement and nesting of the elements 28, 29 and 30 and/or the leader 26, but post-implantation the visualization of the prosthesis 8 can be unobstructed by the radiopaque nature of the elements 28, 29 and 30 and/or the leader 26

The elements 28, 30 or 32 can be filled or coated with an agent delivery matrix known to one having ordinary skill in the art and/or a therapeutic and/or diagnostic agent. The device 24, or any of the parts of the device 24, can be coated with the agents. These agents can include radioactive materials; radiopaque materials, for example gold; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., VIOXX® from Merck & Co., inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (AMP) inhibitors (e.g., tetracycline and tetracycline derivatives) that act early within the pathways of an inflammatory response. Examples of other agents are provided in Walton et al, Inhibition of Prostoglandin $E_2$ Synthesis in Abdominal Aortic Aneurysms, *Circulation*, Jul. 6, 1999, 48-54; Tambiah et al, Provocation of Experimental Aortic Inflammation Mediators and *Chlamydia Pneumoniae, Brit. J. Surgery* 88 (7), 935-940; Franklin et al, Uptake of Tetracycline by Aortic Aneurysm Wall and Its Effect on Inflammation and Proteolysis, *Brit. J. Surgery* 86 (6), 771-775; Xu et al, Sp1 Increases Expression of Cyclooxygenase-2 in Hypoxic Vascular Endothelium, *J. Biological Chemistry* 275 (32) 24583-24589; and Pyo et al, Targeted Gene Disruption of Matrix Metalloprotehtase-9 (Gelatinase B) Suppresses Development of Experimental Abdominal Aortic Aneurysms, *J. Clinical Investigation* 105 (11), 1641-1649 which are all incorporated by reference in their entireties. Once the device 24 is deployed, these agents can provide various benefits such as it promote fusing of the space-occupying elements 28, 30 or 32 to each other or to the surrounding biologic materials (e.g., a collagen coating), and/or ii) promote a thrombogenic response within the sac 10 to stabilize the device 24 and the prosthesis 8, and/or iii) function to promote healing of the aneurysm at the cellular level such as in the case of treating an inflammatory response.

Method of Making

The elements 28, 30 and 32 and the leader 26 can be made from methods known to those having ordinary skill in the art. For example, the elements 28, 30 and 32 can be molded or machined. The embodiments of the device 24 illustrated in FIGS. 10, 11 and 14 can be extruded and then a helical cut in the extrusion can be made by a blade, laser, water jet or hot wire to form the leaders 26 and 26a.

The elements 28, 30 and 32 can be molded, machined, or mounted onto the leader 26. The elements 28, 30 and 32 can be mourned to the leader 26 with an interference fit, for example by tying knots in the leader 26 surrounding the elements 28, 30 and 32 mounting the elements 28, 30 and 32 onto the ferrule 56 which is already crimped onto the leader 26. The elements 28, 30 and 32 can be pressure fitted onto the leader 26, for example by crimping the elements 28, 30 and 32 onto the leader 26, snapping snap-together sections 44 and 46 onto the leader 26, or distortion mounting by heating the elements 28, 30 and 32 to a threshold of thermal distortion. The elements 28, 30 and 32 can be glued onto the leader 26 with a biocompatible adhesive (e.g., cyanoacrylate), bonded ultrasonically; or heat bonded (e.g., melting, heat welding). Each section 44 or 46 can be attached to the other section 44 or 46 with any of the above methods.

Any part of the device 24, or the device 24 as a whole after assembly, can be coated by dip-coating or spray-coating methods known to one having ordinary skill in the art. One example of a method used to coat a medical device for vascular use is provided in U.S. Pat. No. 6,358,556 by Ding et al. and hereby incorporated by reference in its entirety. Time release coating methods known to one having ordinary skill in the art can also be used to delay the release of an agent in the coating, for example inclusion of a collagen matrix in the coating.

Method of Use

Before using the device 24, the sac 10 can be cleaned of debris (e.g., thrombi), for example by mechanically macerating the debris or using a lytic agent (e.g, Urokinase, for example Abbokinase® from Abbott Laboratories, Abbott Park, Ill.). Examples of devices capable of performing pharmomechanical treatment—that can be delivered to the sac 10 through the same delivery apparatus as the device 24—are the TRELLIS™ and FINO™ from Bacchus Vascular, Inc. (Santa Clara, Calif.). Use of the device 24 can be performed while using a visualization tool, for example fluoroscopy or computed tomography (CT) scanning. The volume of the sac 10 not filled by debris can be estimated from visual inspection, for example by inspection of images from the visualization tool. Software known to one having ordinary skill in the art can also be used to assist in estimating the volume of the sac 10.

A length of the device 24 can be stored in a sterile package, for example by an individual predetermined length or on a spool, spindle, or in a cartridge. The device volume can be reduced by removing more than enough of the device 24 from the sterile package and then reducing the length of the device 24, for example by cutting the leader 26 or unplugging a poppet 72 from a socket 74. In this way, the device volume can be reduced to the approximate volume of the sac 10 not filled by debris. The device volume can be large enough to substantially fill the vascular site, and the device volume can be small enough to prevent substantial alteration of the natural fluid flow through the prosthesis 8.

Figure 15:
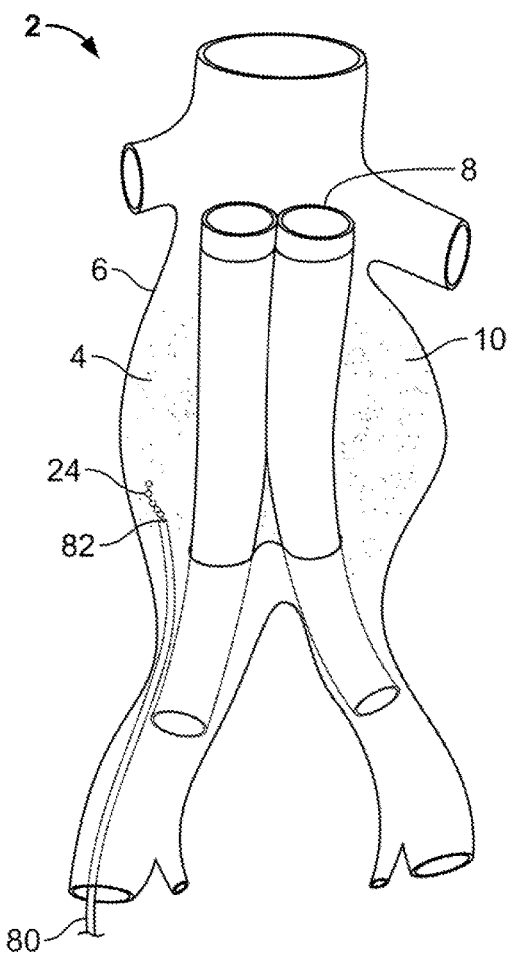
FIG. 15 illustrates an embodiment of the method of implanting the embolization device.

The device 24 can be deployed to the sac 10 using a trans-graft, trans-collateral, trans-sac, or endoluminal procedure. As illustrated in FIG. 15, a catheter 80 with a distal exit 82 can be placed in the aneurysm 4. The distal exit can be placed at the sac 10. The device 24 can then be passed through the catheter 80 and distal exit 82, and can be deployed into the sac 10.

Figure 16:
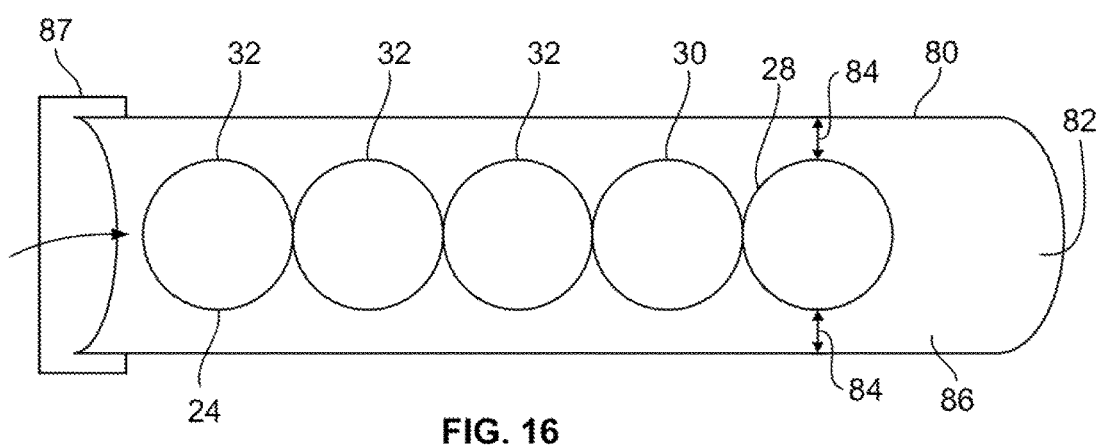
FIG. 16 is a cut-away view of a catheter carrying an embodiment of the embolization device.

As illustrated in FIG. 16, a catheter clearance 84 is the distance between the device 24 and an inner wall 86 of the catheter 80. The inner walls 86 of the catheter 80 can act as a guide for the device 24 during deployment. If the catheter clearance 84 is too large, the inner walls 86 of the catheter 80 can no longer act as a guide and the device 24 can "boxcar" within the catheter 80. Boxcarring occurs when the elements 28, 30 and 32 bunch up and impair delivery, preventing an upstream element from transmitting force to a downstream element in a direction substantially parallel with the inner walls 86. The maximum catheter clearance 84 before the elements 28, 30 and 32 can begin to boxcar is the "critical clearance". The critical clearance can be about 80% of the element outer diameter 38, more narrowly about 26% of the element outer diameter, yet more narrowly about 12% of the element outer diameter 38.

An end of the catheter 80 can have a valve 87 to minimize or completely prevent backflow of body fluids or other leakage and improve the connection of other devices to the end of the catheter 80. Use of the valve 87 at the end of the catheter 80 is understood to one having ordinary skill in the art. The valve 87 can be, for example, a hemostasis valve (e.g., from Cook, Inc., Bloomington, Ind.).

Figure 17:
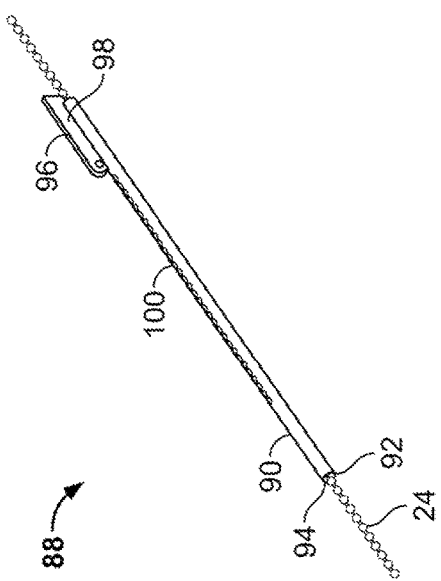

FIG. 17 illustrates a ratcheting driver 88 having a feed tube 90 that can be used to control the device 24 during deployment. The device 24 can pass through a channel 92 in the feed tube 90. An end 94 of the feed tube 90 can connect to the valve 87 or the catheter 80. The driver 88 can have a spring-loaded handle 96. The handle 96 can be connected to a ram 98. The handle 96 can move along a track 100 in the feed tube 90. When the handle 96 is pushed, the ram 98 can press the device 24 forward through the channel 92. When the handle 96 is released, the handle 96 can revert to a starting position and prevent the device 24 from moving backwards through the channel 92.

Figure 18:
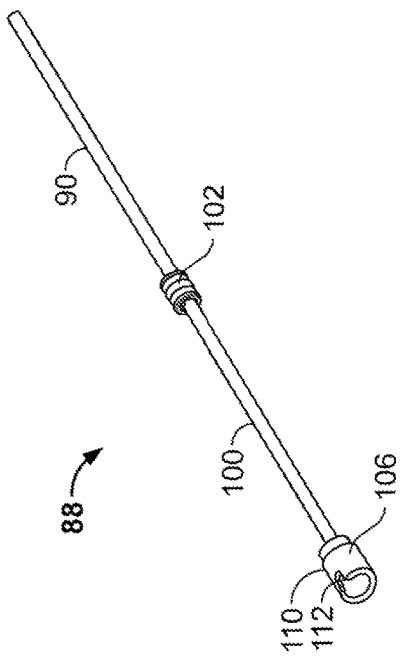
FIGS. 17 and 18 illustrate embodiments for the drivers used to deploy the embolization device.
Figure 19:
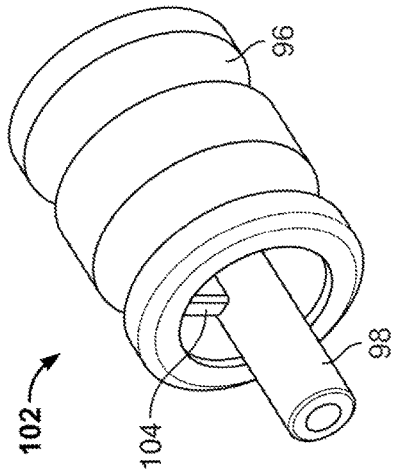
FIG. 19 illustrates an embodiment of the slider from the driver.
Figure 21:
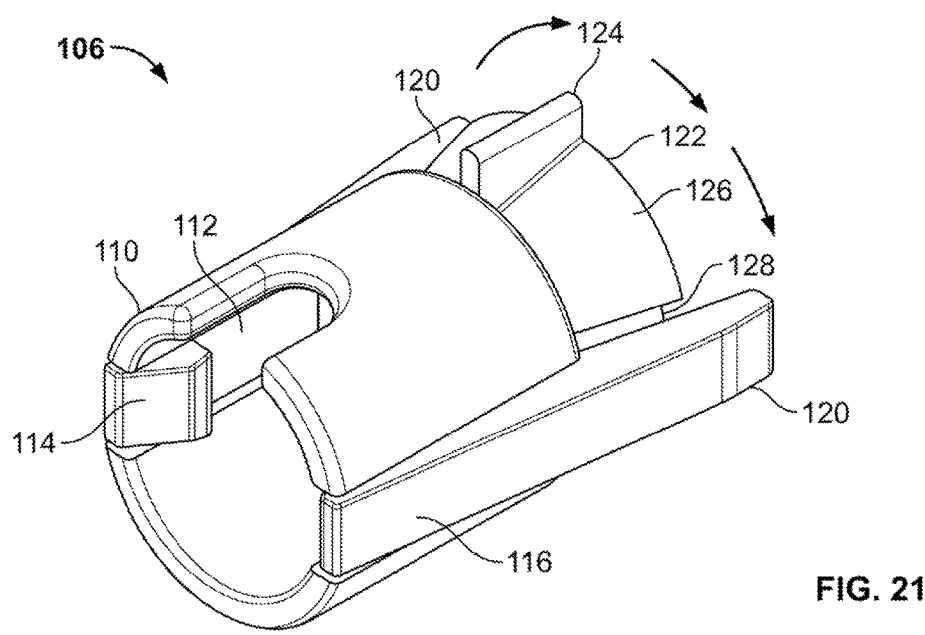
FIG. 21 illustrates an embodiment of the connector in an unlocked configuration.
Figure 23:
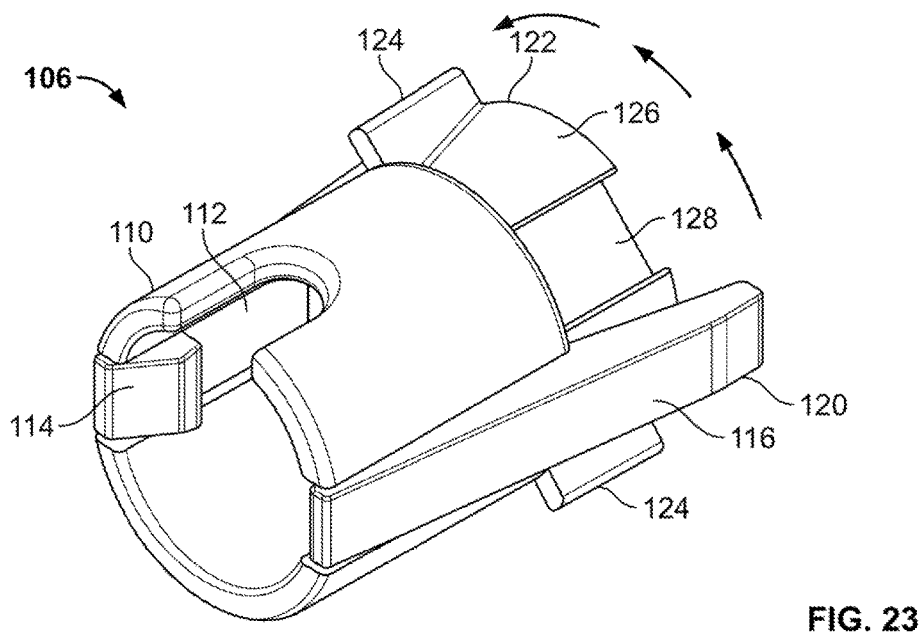
FIG. 23 illustrates the connector of FIG. 21 in a locked configuration.
Figure 22:
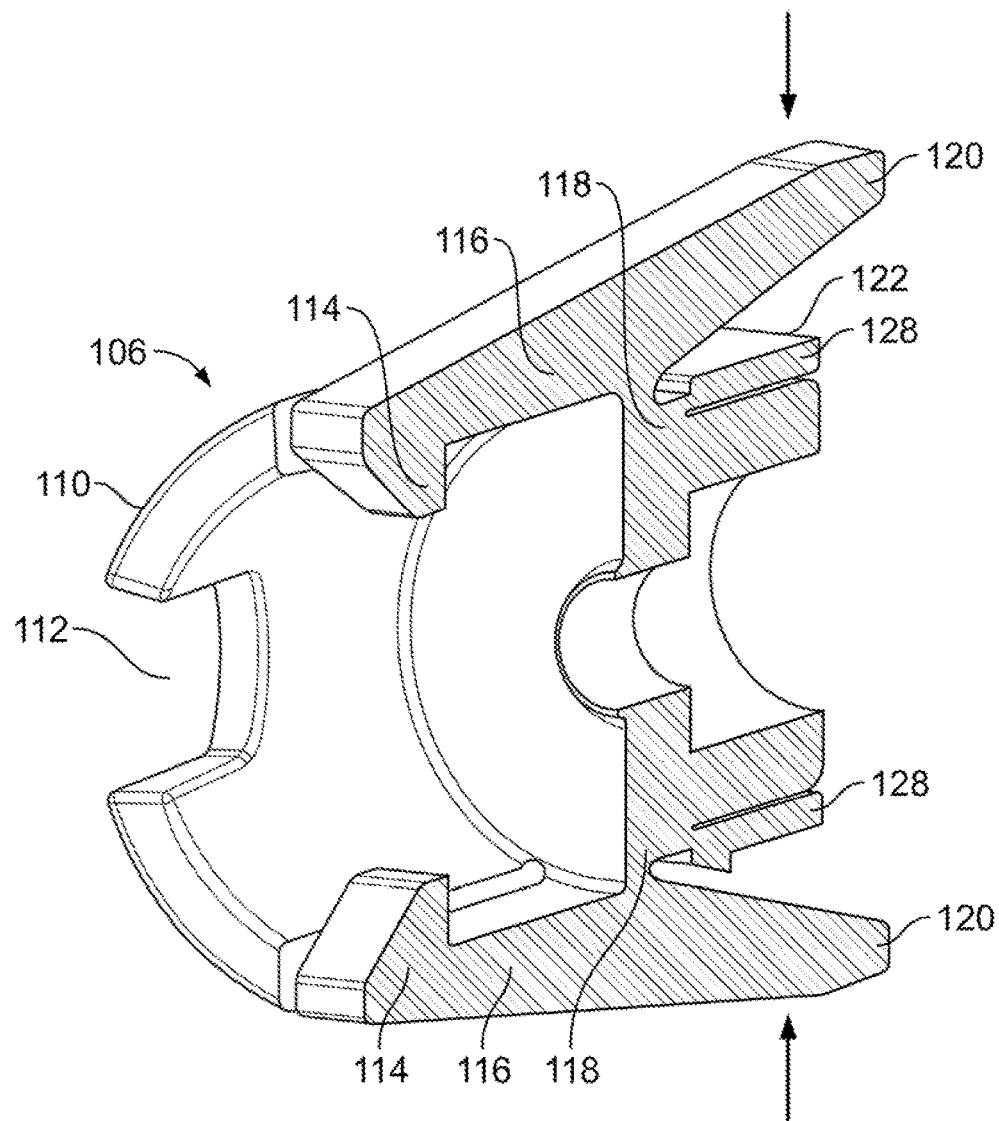
FIG. 22 is a cross-sectional view of the connector of FIG. 21.
Figure 24:
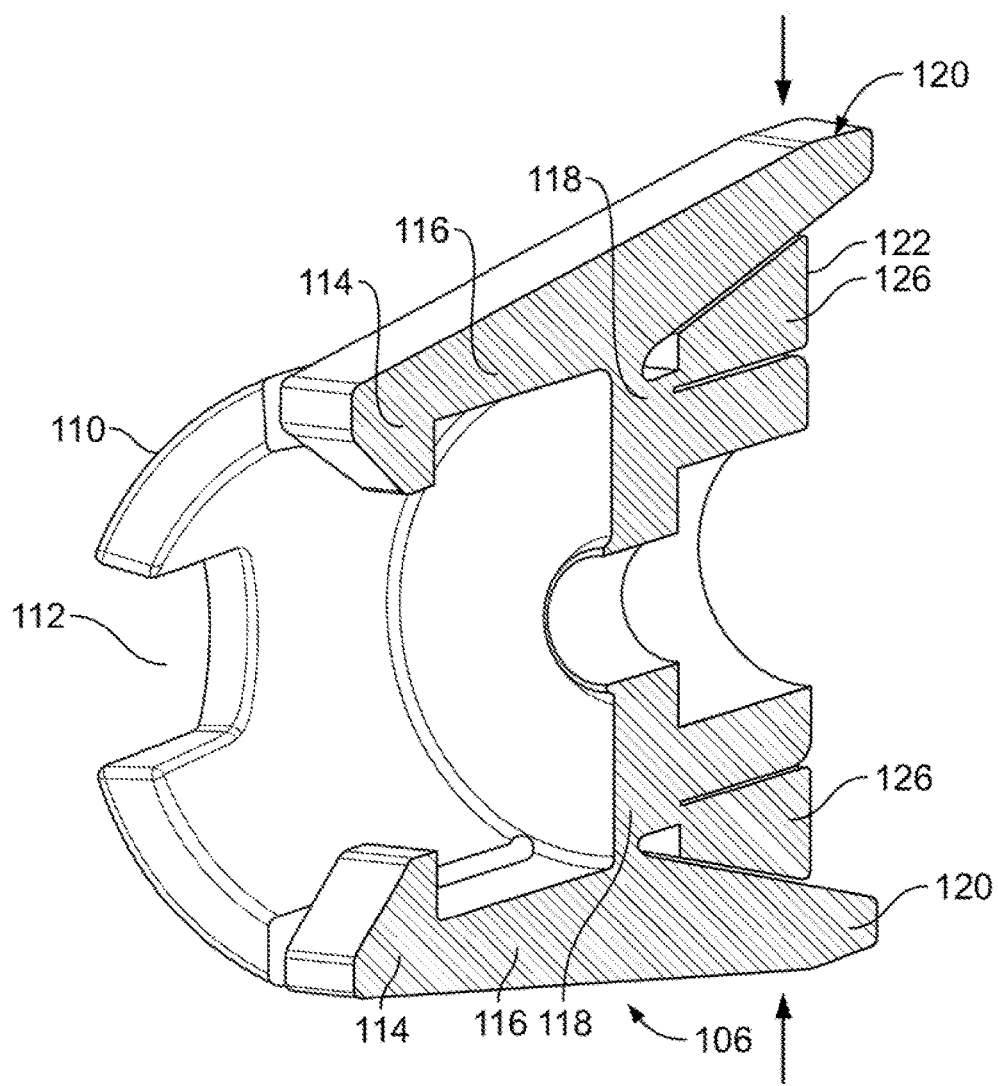
FIG. 24 is a cross-sectional view of the connector of FIG. 23.

FIG. 18 illustrates a sliding driver 88 having a slider 102. The slider 102, illustrated in FIG. 19, can have a rib 104 that can engage the track 100. The slider 102 can abut and deliver a force to the end of the device 24 when the device 24 is in the channel 92.

The geometries of the elements 28, 30 and 32 of the device 24 and the properties of the leader 26 can benefit delivery of the device 24. As the slider 102 delivers force to the end of the device 24, the leader 26 can buckle or flex, allowing elements 28, 30 and 32 to approximate and transmit force from one element 28, 30 or 32 to the other elements 28, 30 or 32, thereby giving the device 24 sufficient column strength to move through the channel 92.

Figure 20:
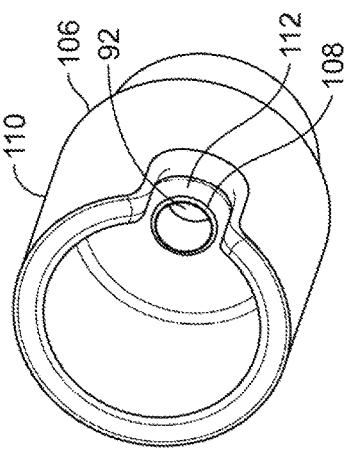
FIG. 20 illustrates an embodiment of the connector.

As illustrated in FIG. 20, a connector 106 at the end 94 of the feed tube 90 can have a lipped hub 108 and a collar 110. The lipped hub 108 can feed into the valve 87 or the opening of a channel in the catheter 80. The collar 110 can fit over the valve 87 or the end of the catheter 80 that joins with the feed tube 90, or the collar 110 can join with another intermediary device between the catheter 80 or the valve 87 and the feed tube 90. The connector 106 can have a check port 112 in the collar 110.

FIGS. 21-24 illustrate an embodiment of the connector 106 that can lock to, and unlock from, the catheter 80. A first end of the connector 106 can have a latch 114 that can form a friction or interference fit with the valve 87 or the catheter 80 (not shown) when the valve 87 or the catheter 80 is loaded into the collar 110 past the latches 114. The latches 114 can be rigidly attached to lever arms 116. The lever arms 116 can be attached to the connector 106 at an attachment location 118 so that the position of the lever arms 114 forces the latches 114 to form the friction or interference fit with the valve 87 or the catheter 80 when no external forces are applied to the lever arms 116. A second end of the lever arm 116 can also have a press tab or button 120.

When a force (shown by arrows in FIG. 22) is applied to the buttons 120, the lever arms 116 can rotate around the attachment location 118, removing the friction or interference fit between the latches 114 and the valve 87 or the catheter 80.

The connector 106 can have a lock 122 that can be rotatably attached to the remainder of the connector 106.

Tabs 124 can protrude from the lock 122. The tabs 124 can be used to aid rotation (shown by arrows in FIGS. 21 and 23) of the lock 122 relative to the remainder of the connector 106, and to provide an interference fit to prevent the lock 122 from turning from one lever arm 114 past the next lever arm 114. The lock 122 can have a thick portion 126 and a thin portion 128.

The lock 122 can be rotated to position the thick portion 126 between the lever arms 116 and a retaining wall 130 (shown in FIGS. 23 and 24), minimizing the rotation of the lever arms 116 and preventing the removal of the friction or interference fit between the latches 114 and the valve 87 or the catheter 80. With the lock 122 in this position, the valve 87 or the catheter 80 can be locked to the connector 106.

The lock 122 can be rotated to position the thin portion 128 between the lever arms 116 and the retaining wall 130 (shown in FIGS. 21 and 22), allowing substantially free rotation of the lever arms 116 and enabling removal of the friction or interference fit between the latches 114 and the valve 87 or the catheter 80. With the lock 122 in this position, the valve 87 or the catheter 80 can be unlocked and removed from the connector 106.

The driver 88 can be integrated with the sterile package (e.g., individual predetermined length, spool, spindle, or cartridge) loaded with the device 24. A new package loaded with the device 24 can replace or be swapped for an old package at the connector 106.

The device 24 can be visualized by the visualization tool before, during and after the device 24 has been deployed. After the device 24 has been deployed, any agents in or on the device 24 can elute into the tissue and fluids. The vascular prosthetic 8 can be implanted before, during or after the device 24 is deployed.

It is apparent to one skilled in the art that various changes and modifications can be made to this disclosure, and equivalents employed, without departing from the spirit and scope of the invention.

We claim:

1. A system for treating an aneurysm comprising:
   a catheter having a distal exit, wherein the distal exit is placeable between an outer surface of a prosthesis and a wall of the aneurysm when the catheter is in a deployed configuration; and
   a material passable through the distal exit of the catheter such that the material is deployable between the outer surface of the prosthesis and the wall of the aneurysm, wherein the system has a first configuration and a second configuration, wherein at least a portion of the material is in the distal exit of the catheter in the first configuration, and wherein the at least a portion of the material contacts the outer surface of the prosthesis in the second configuration.

2. The system of claim 1, wherein the prosthesis bifurcates at a bifurcation point into a first leg and a second leg, wherein a first length of a longitudinal axis of the catheter is parallel to a length of a longitudinal axis of at least the first leg or the second leg of the prosthesis, wherein the catheter is configured to deploy the material such that the material exits the catheter in a direction parallel to a second length of the longitudinal axis of the catheter, wherein the distal exit of the catheter is superior to the bifurcation point when the catheter is in the deployed configuration, wherein the material further comprises a coating, wherein the coating is configured to cover the material, and wherein the coating is an agent.

3. The system of claim 1, wherein the prosthesis bifurcates at a bifurcation point into a first leg and a second leg, and wherein a first length of a longitudinal axis of the catheter is parallel to a length of a longitudinal axis of at least the first leg or the second leg of the prosthesis.

4. The system of claim 3, wherein the distal exit of the catheter is superior to the bifurcation point when the catheter is in the deployed configuration.

5. The system of claim 1, wherein the catheter is configured to deploy the material such that the material exits the catheter in a direction parallel to a length of the longitudinal axis of the catheter.

6. The system of claim 1, wherein the material comprises a coating, wherein the coating is configured to cover the material, wherein the coating is an agent, and wherein the agent is at least one of a therapeutic agent and a diagnostic agent.

7. The system of claim 1, wherein the material is configured to coil when the material deploys between the outer surface of the prosthesis and the wall of the aneurysm.

8. The method of claim 1, wherein the distal exit comprises an opening having a cross-sectional area, and wherein the material substantially fills the opening when the system is in the first configuration.

* * * * *